(12) United States Patent
Ventimiglia et al.

(10) Patent No.: US 8,933,114 B2
(45) Date of Patent: Jan. 13, 2015

(54) POLYMORPHIC FORMS OF ASENAPINE MALEATE AND PROCESSES FOR THEIR PREPARATION

(75) Inventors: Gianpiero Ventimiglia, Francavilla Fontana (IT); Giuseppe Barreca, Montevecchia (IT); Domenico Magrone, Verona (IT)

(73) Assignee: Chemo Iberica, S.A., Barcelona (ES)

( * ) Notice: Subject to any disclaimer, the term of this patent is extended or adjusted under 35 U.S.C. 154(b) by 0 days.

(21) Appl. No.: 13/993,140

(22) PCT Filed: Dec. 12, 2011

(86) PCT No.: PCT/EP2011/072495
§ 371 (c)(1),
(2), (4) Date: Jun. 11, 2013

(87) PCT Pub. No.: WO2012/080195
PCT Pub. Date: Jun. 21, 2012

(65) Prior Publication Data
US 2013/0267574 A1    Oct. 10, 2013

(30) Foreign Application Priority Data

Dec. 13, 2010   (EP) ..................................... 10194747

(51) Int. Cl.
*C07D 491/044*      (2006.01)

(52) U.S. Cl.
CPC .................................. *C07D 491/044* (2013.01)
USPC .......................................... 514/410; 548/421

(58) Field of Classification Search
CPC .................................................... C07D 491/044
USPC .......................................... 514/410; 548/421
See application file for complete search history.

(56) References Cited

U.S. PATENT DOCUMENTS

2007/0027134 A1   2/2007  Heeres
2008/0009619 A1   1/2008  Kemperman et al.

FOREIGN PATENT DOCUMENTS

| WO | 95/23600 | 9/1995 |
| WO | 2006/106135 | 10/2006 |
| WO | 2008/040816 | 4/2008 |

OTHER PUBLICATIONS

Caira, M. R., "Crystalline Polymorphism of Organic Compounds", Topics in Current Chemistry, 1998, vol. 198, pp. 164-208.
Funke, C.W. et al., "Physico-chemical Properties and Stability of trans-5-Chloro-2-methyl-2,3,3a, 12b-tetrahydro-1H-dibenz[2,3 : 6,7]oxepino {4,5-c]pyrrolidine Maleate", Drug Research, 1990, vol. 40 (I), No. 5., pp. 536-539.

*Primary Examiner* — Shawquia Jackson
(74) *Attorney, Agent, or Firm* — Fish & Tsang LLP

(57) ABSTRACT

Are disclosed new crystalline forms of asenapine maleate, useful in the production of pharmaceutical formulations for the treatment of diseases of the central nervous system, in particular schizophrenia; processes for the production of these new crystalline forms are also disclosed.

32 Claims, 6 Drawing Sheets

POLYMORPHIC FORMS OF ASENAPINE MALEATE AND PROCESSES FOR THEIR PREPARATION

FIELD OF THE INVENTION

Figure 1:
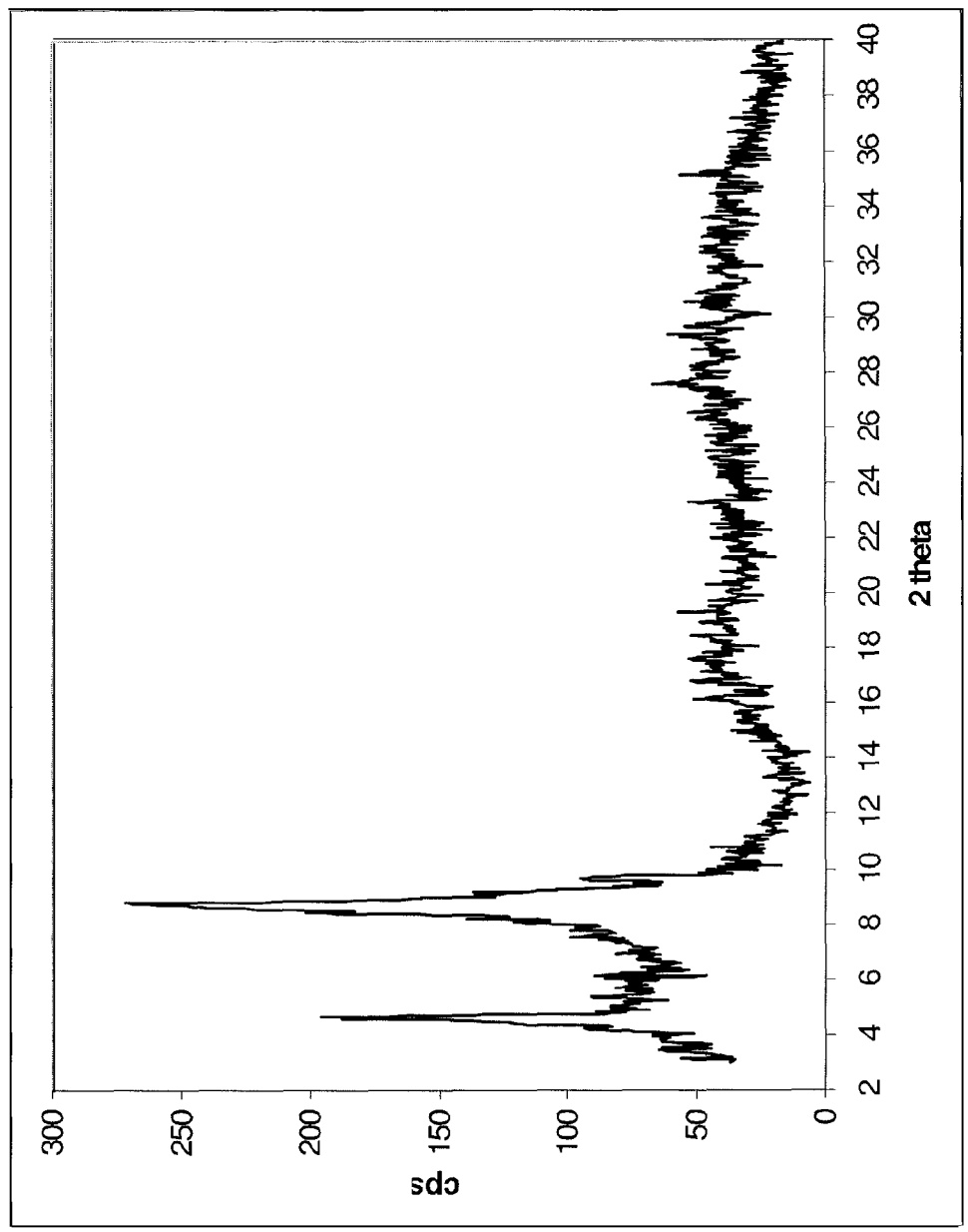

The present invention relates to polymorphic forms of asenapine maleate and processes for preparation thereof.

BACKGROUND OF THE INVENTION

Asenapine, whose chemical name is (3aR,12bR)-5-chloro-2-methyl-2,3,3a,12b-tetrahydro-1H-dibenzo[2,3:6,7]oxepino[4,5-c]pyrrole, is a compound of formula (I):

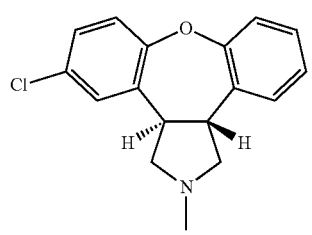

(I)

Asenapine, disclosed in U.S. Pat. No. 4,145,434, is used in the treatment of diseases of the central nervous system, in particular schizophrenia. It has been established that asenapine is a very potent dopamine and a serotonin antagonist with antipsychotic activity.

Asenapine is marketed as maleate salt under the trade name SAPHRIS® (a registered trademark of N.V. Organon, a subsidiary of Merck & Co., Inc.).

As it is well known to those skilled in the art, the crystalline form and morphology of a solid form of a pharmaceutical compound may greatly influence its physicochemical properties, such as stability, rate of dissolution, bioavailability, and the like.

Substances are known which only appear in a single crystal form; other substances, on the other hand, can exist in two, three or even more crystal modifications. The property of some molecules and molecular complexes to assume more than one crystalline or amorphous form in the solid state is known as polymorphism, and the different forms of a compound are referred to as polymorphs. In general, polymorphism is caused by the ability of the molecule of a compound to change its conformation or to form different inter- and intra-molecular interactions, particularly hydrogen bonds, which is reflected in different atom arrangements in the crystal lattices of different polymorphs. Accordingly, polymorphs are distinct solids sharing the same molecular formula, having distinct advantageous and/or disadvantageous physical properties compared to other forms in the polymorph family.

From a physical point of view, once salts of pharmaceutical compounds have been isolated, they can be characterized by their thermal behaviour. Thermal behavior is measured in the laboratory by such techniques as Differential Scanning calorimetry (DSC) and can be used to distinguish among polymorphs. Melting points, glass transitions, crystallinity, solvates, and/or presence of polymorphic behaviour can be evidenced by multiple endotherms, poorly defined endotherms, and endotherms near the boiling point of solvents. The potential for polymorphism may also give rise to distinct spectroscopic properties that may be detectable by X-Ray Powder Diffraction (XRPD) analysis.

The relevant polymorphism of an organo-chemical substance is always unpredictable in respect of the number of crystal modifications, the stability thereof and their behaviour in a living organism.

The different polymorphs of a substance possess different energies of the crystal lattice and, thus, they show different physical properties of the solid state such as form, density, melting point, colour, stability, dissolution rate, milling facility, granulation, compacting etc. These differences in morphology and polymorphism may have drastic effects on the flowability of the milled solid (flowability affects the ease with which the material is handled during processing into a pharmaceutical product; when particles of the powdered compound do not flow past each other easily, a formulation specialist must necessitate the use of glidants); on development, transport stability and storage stability of individual administration forms; on the ability to produce different administration forms and on their application; on the solubility in polar or non-polar, protic or aprotic solvents, in aqueous solution, in the gastric juices or in blood serum; and finally on bio-availability. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. Other important properties of polymorphic forms relate to the ease of processing the form into pharmaceutical dosages, as the tendency of a powdered or granulated form to flow and the surface properties that determine whether crystals of the form will adhere to each other when compacted into a tablet.

The discovery of novel polymorphic forms of a pharmaceutically useful compound provides a new opportunity to improve the performance characteristics of a pharmaceutical product. It enlarges the repertoire of materials that a formulation scientist has available for designing a pharmaceutical dosage form, or a drug with a targeted release profile, or other desired characteristics, such as flowability and suitable rate of dissolution in aqueous fluid. Therefore, there is an ongoing research effort aimed to identifying new forms of known compounds, in the quest for ever better pharmacological properties (a lower required dosage, a faster action, . . . ).

Asenapine maleate was first obtained as anhydrous monoclinic form (also known as Form H), as described by Funke et al. in *Arzneim.-Forsch/Drug Res.*, 40:536-539 (1999). This known form has a melting point of 141-145° C.

WO 2006/106135 discloses a new crystalline form of asenapine maleate, herein referred to as orthorhombic form or Form L, whose melting point is in the range 138-142° C.

WO 2008/040816 discloses an amorphous form of asenapine maleate, prepared via spray-drying or freeze-drying processes. However, the present inventors have found that an amorphous form prepared by means of freeze-drying is not stable, and spontaneously converts into Form H upon standing.

WO 95/23600 describes the production of a sublingual formulation of asenapine maleate. It is known that the particle size of a drug substance influences biopharmaceutical properties of the drug itself; thus, according to this document, it is desired to employ the salt in the form of powder with a small particle size, preferably about 100 μm or less. In order to reduce the particle size of the crystals, a micronization step is applied, starting from form H (monoclinic). However, some drawbacks are associated with the micronization process, since an unpredictable mixture of Form H and Form L is obtained starting with the monoclinic form. As any given form has its own physicochemical properties, a mixture of polymorphic forms of a compound gives rise to unpredictable overall properties of a formulated pharmaceutical product containing said mixture, thus affecting the effectiveness of the medicament.

On the basis of these considerations, preparation and characterization of novel solid forms of asenapine maleate is desirable.

An object of the present invention is to provide novel anhydrous and non solvate solid forms of asenapine maleate and processes for preparing them.

SUMMARY OF THE INVENTION

The present invention provides novel anhydrous crystalline forms of asenapine maleate, and processes for preparing them.

In a first aspect thereof, the invention provides novel polymorphic forms of asenapine maleate, herein designated as Form G, Form G1 and Form G2, respectively.

Polymorphic Form G of asenapine maleate is characterized by an XRPD pattern comprising peaks at 4.5°, 8.7°, and 27.7° 2θ.

Polymorphic Form G1 of asenapine maleate is characterized by an XRPD pattern comprising peaks at 10.1°, 10.7°, 12.1°, 17.1°, 20.0°, 22.4°, and 24.4° 2θ.

Polymorphic Form G2 of asenapine maleate is characterized by an XRPD pattern comprising peaks at 6.6°, 9.2°, 10.4°, 13.2°, 16.8°, 18.5°, 20.1°, 21.2°, and 21.8° 2θ.

Any values of 2θ angles reported above, in the following description and in the claims, must be intended as given with an approximation of ±0.2.

In a second aspect thereof, the invention provides processes for preparing said polymorphic forms of asenapine maleate.

A first possible process for preparing Form G of asenapine maleate comprises the steps of:
  a) dissolving asenapine maleate in a solvent that is a mixture of water and an alcohol;
  b) adding a polyoxotungstate as seed; and
  c) recovering the solid product.

A second possible process for preparing Form G of asenapine maleate comprises the steps of:
  d) suspending asenapine maleate in an alcohol;
  e) heating the suspension in order to obtain a clear solution;
  f) seeding with Form G of asenapine maleate;
  g) cooling down the solution in order for Form G to crystallize; and
  h) recovering the solid product.

A process for preparing Form G1 of asenapine maleate comprises the steps of:
  i) suspending asenapine maleate in an alcohol;
  j) heating the suspension in order to obtain a clear solution;
  k) cooling down the solution in order for Form G1 to crystallize; and
  l) recovering the solid product.

In a possible variant of the process for preparing Form G1, a further step, k'), is carried out between said steps j) and k), consisting in seeding the solution obtained in step j) with Form G1 of asenapine maleate.

A first possible process for preparing Form G2 of asenapine maleate comprises the steps of:
  m) suspending asenapine maleate in a mixture toluene/tetrahydrofuran;
  n) heating the suspension in order to obtain a clear solution;
  o) cooling down the solution in order for Form G2 to crystallize; and
  p) recovering the solid product.

A second possible process for preparing Form G2 of asenapine maleate comprises the steps of:
  q) suspending asenapine maleate in an alcohol;
  r) heating the suspension in order to obtain a clear solution;
  s) seeding with Form G2 of asenapine maleate;
  t) cooling down the solution in order for Form G2 to crystallize; and
  u) recovering the solid product.

BRIEF DESCRIPTION OF THE DRAWINGS AND INSTRUMENTAL SKILLS

Figure 2:
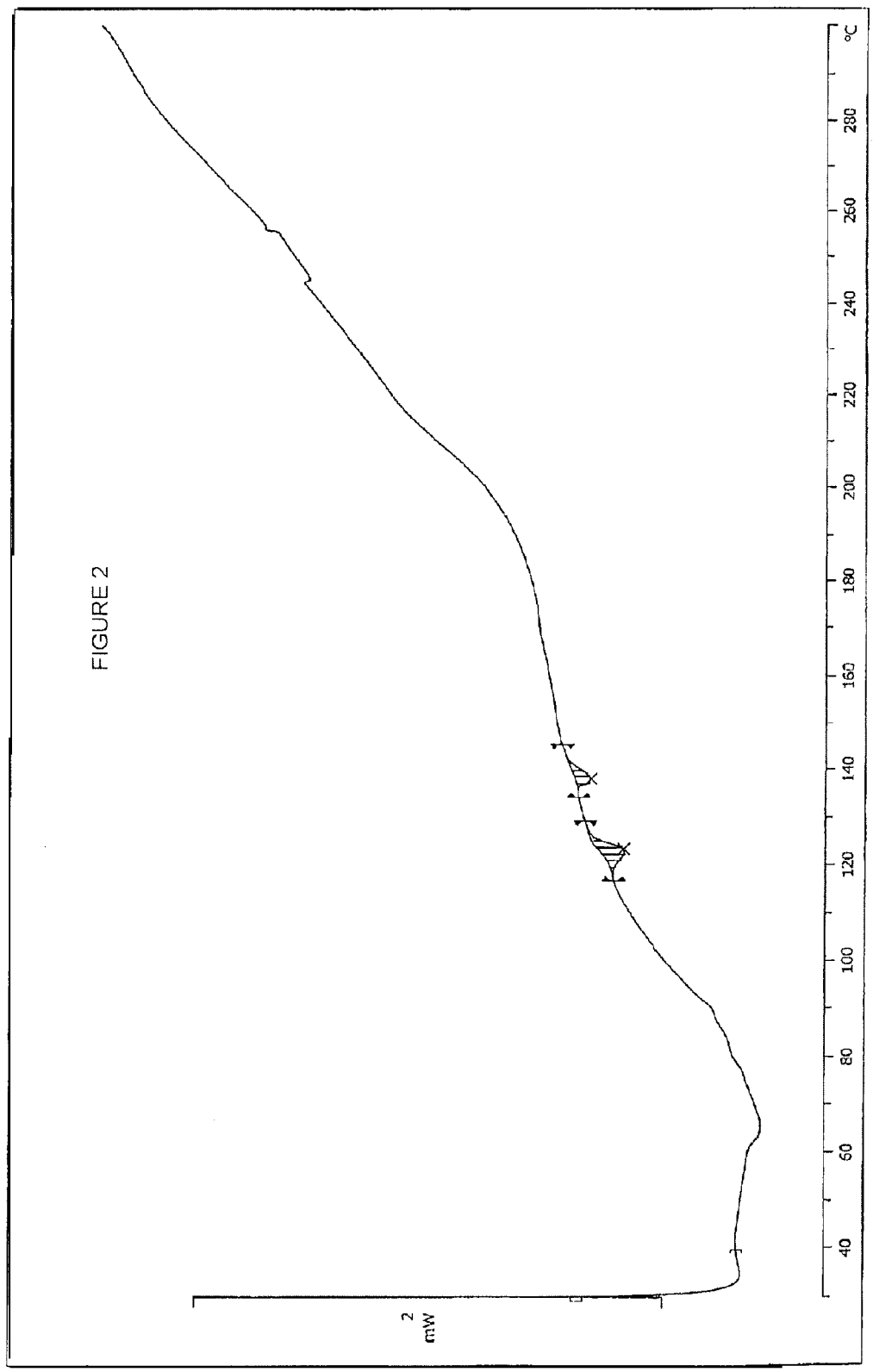
Figure 3:
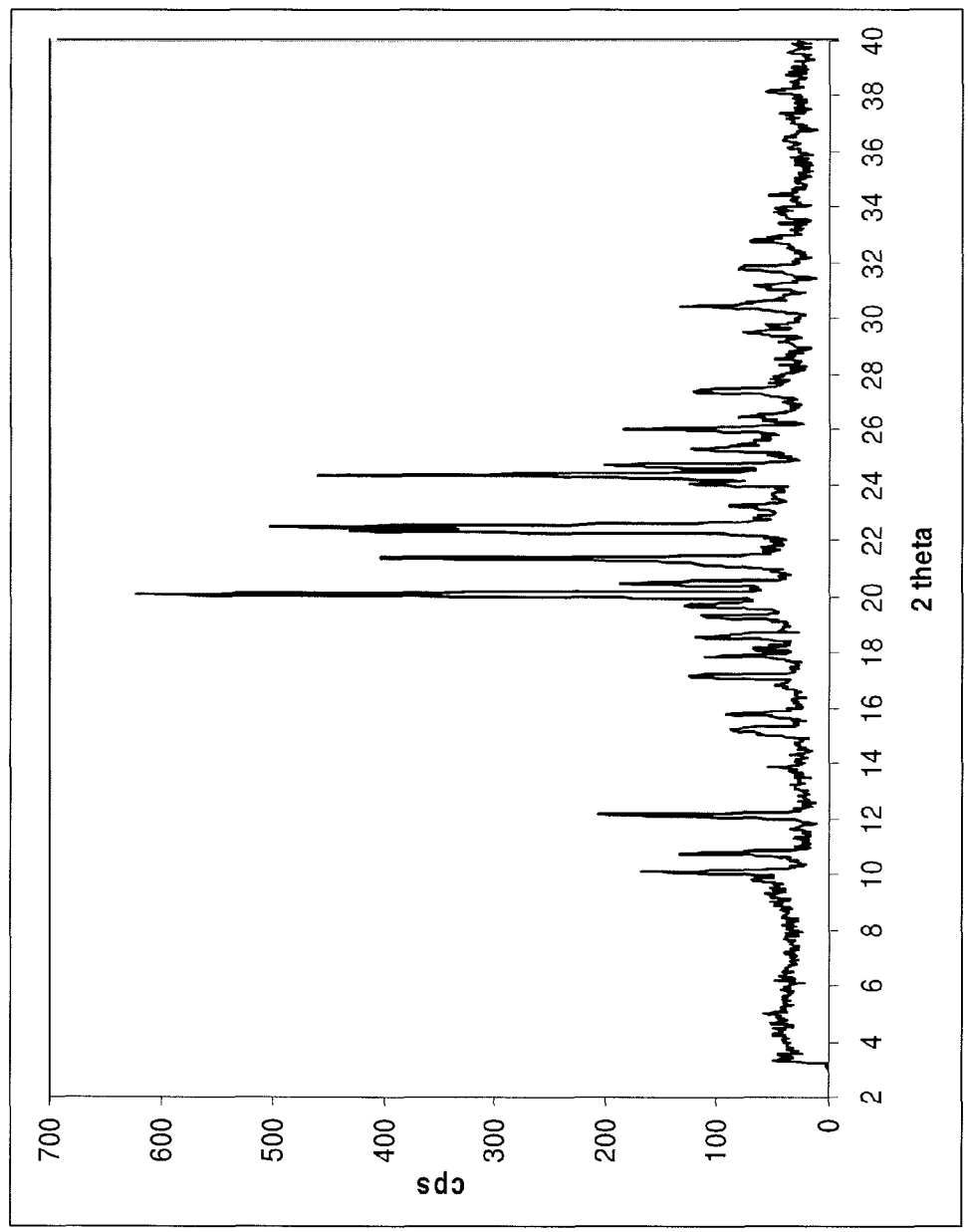
Figure 4:
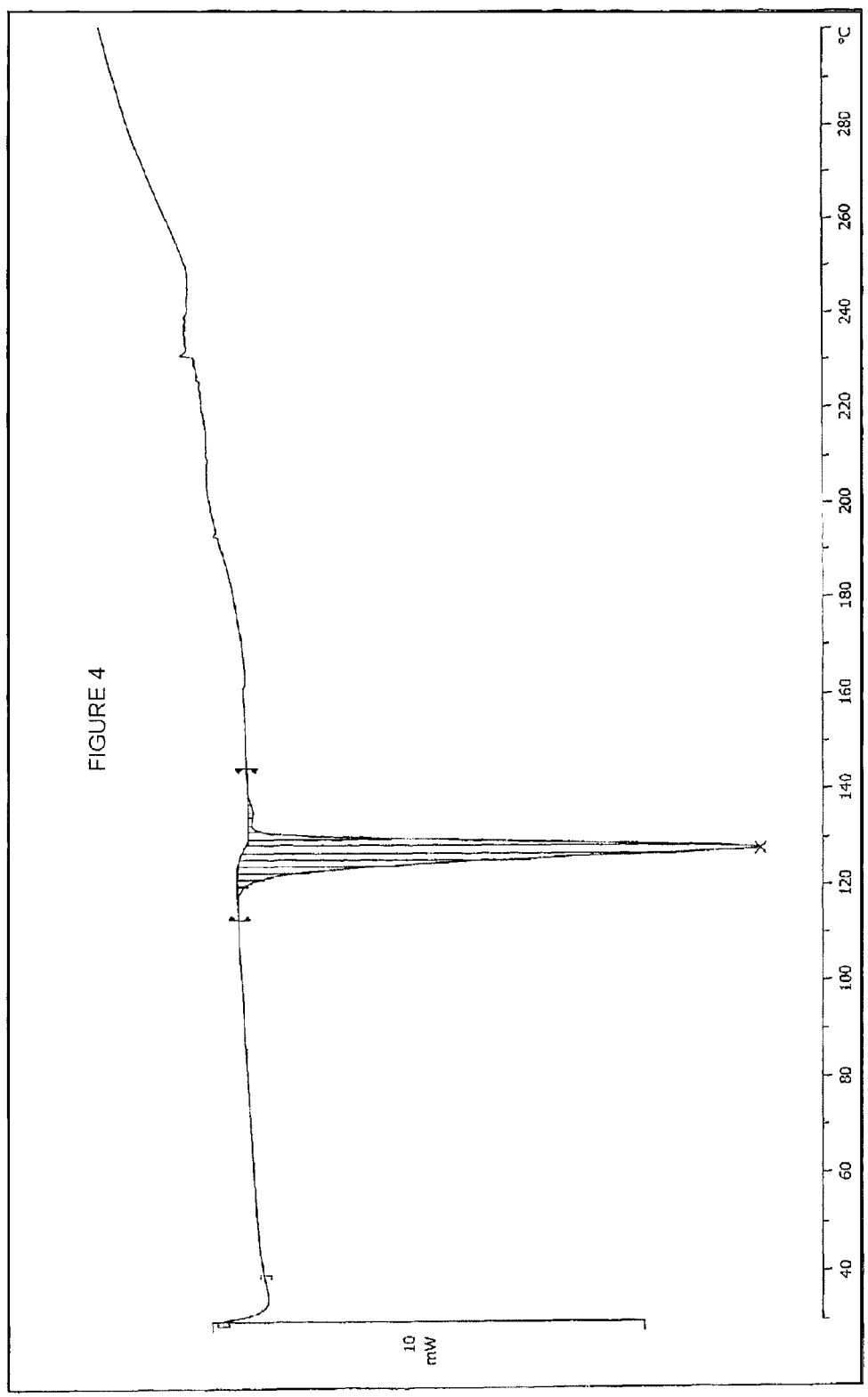
Figure 5:
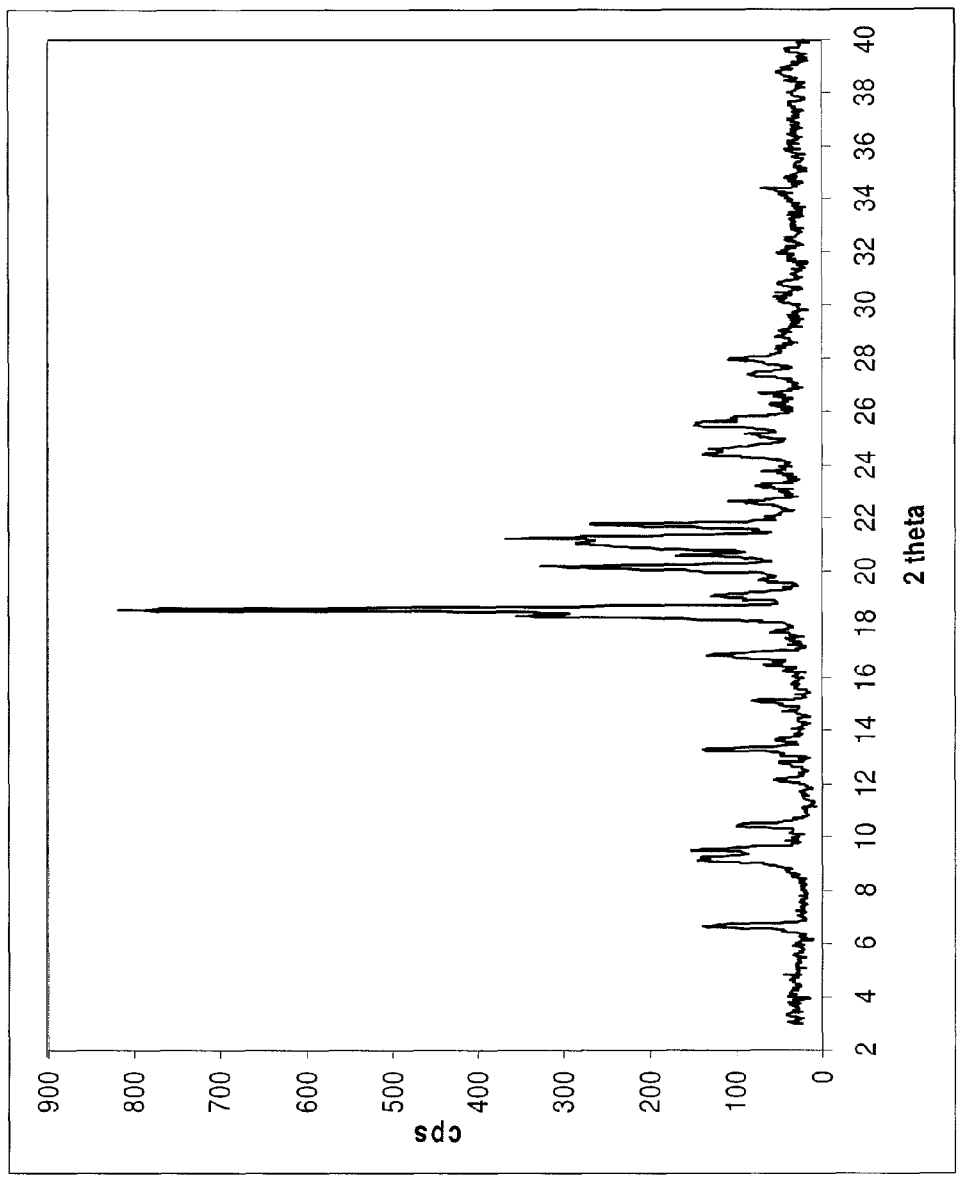
Figure 6:
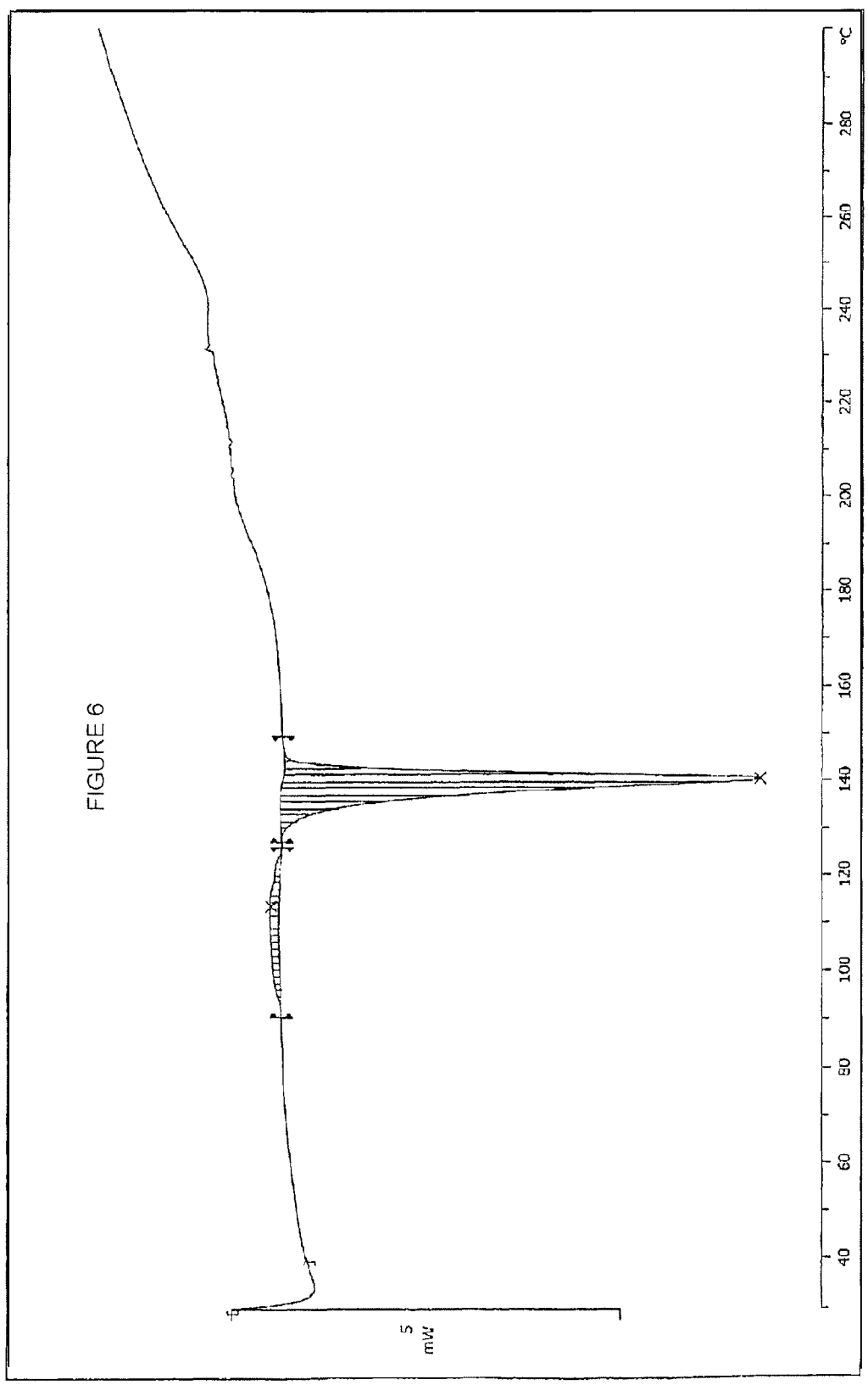

FIG. 1 provides XRPD spectrum of asenapine maleate Form G;

FIG. 2 provides DSC thermogram of asenapine maleate Form G;

FIG. 3 provides XRPD spectrum of asenapine maleate Form G1;

FIG. 4 provides DSC thermogram of asenapine maleate Form G1;

FIG. 5 provides XRPD spectrum of asenapine maleate Form G2;

FIG. 6 provides DSC thermogram of asenapine maleate Form G2.

DETAILED DESCRIPTION OF THE INVENTION

The inventors have surprisingly found that asenapine maleate may be prepared in a manner that results in novel polymorphic forms, that have been designated as Forms G, G1 and G2, respectively. These novel forms of asenapine maleate are found to be stable at room temperature, reproducible and suitable for pharmaceutical dosage forms. They can be prepared with efficient and economic processes particularly suited to large-scale preparation.

All terms used in the rest of the description, unless stated otherwise, shall be understood in their ordinary meaning as known in the art. Other more specific definitions for certain terms as used in the present application are as set forth below and are intended to apply uniformly throughout the specification and claims unless an otherwise expressly set out definition provides a broader meaning.

The term "about" encompasses the range of experimental error that may typically occurs in a measurement.

The term "polyoxotungstate" means a polyatomic anion, that consists of three or more tungsten oxyanions linked together by shared oxygen atoms to form a tridimensional cluster framework.

The term "excipient" means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition into a discrete article such as a tablet, solution, or the like.

The term "pharmaceutical dosage forms" refers to physically discrete units suitable as unitary dosages for human subjects and other mammals, each unit containing a predetermined quantity of active material calculated to produce the desired therapeutic effect, in association with a suitable pharmaceutical excipient.

By "weight/volume ratio" is meant the amount of a solute expressed in grams per 1 mL of pure solvent.

XRPD analysis and DSC thermal analysis were used to characterize polymorphic forms of asenapine maleate. DSC tests referred to in the following description are carried out at a scanning rate of 10° C./min and under an inert atmosphere;

besides, in the following description, the values of lower and upper limits of temperature ranges in which DSC features occur are to be intended as given with an approximation of ±0.5° C.

Form G of asenapine maleate has an XRPD spectrum and a DSC thermogram as depicted respectively in FIG. 1 and FIG. 2.

Form G of asenapine maleate is characterized by an XRPD pattern comprising peaks at 4.5°, 8.7°, and 27.7° 2θ and by a DSC thermogram showing a first endothermic feature between 116.8 and 129.2° C. and a second endothermic feature between 134.3 and 145.4° C.

Form G of asenapine maleate can be prepared according to a first process, comprising steps a) to c) set forth above.

In step a), asenapine maleate is dissolved in a mixture of water and an alcohol at a suitable temperature, preferably in a range of about 0° C. to about 30° C. The alcohol may selected from a group consisting of methanol, ethanol, 1-propanol, 2-propanol, 1-butanol and 2-butanol and their mixtures; preferably, it is chosen among methanol, ethanol and 2-propanol; and more preferably, it is one of methanol or ethanol. Preferably, the water/alcohol ratio in the solvent is comprised between about 5% to about 10% volume/volume. The amount of asenapine maleate dissolved in the solvent in this step may vary in a wide range. Preferably, however, asenapine maleate is dissolved at a weight/volume ratio comprised between about 1:1 and about 1:2; working with more diluted solutions leads to lower overall yields and worse economics of the process.

In step b) of this process, the solution obtained in step a) is seeded with a crystalline polyoxotungstate. Preferably, the polyoxotungstate is a salt of formula $M_6W_{12}O_{39}\cdot nH_2O$, wherein M is an alkali metal cation selected among lithium, sodium and potassium, and preferably is sodium or potassium. The polyoxotungstate is preferably in the form of monohydrate adduct, n=1. Preferably, the polyoxotungstate is added to the solution in a weight ratio of about 0.5% to about 1.0% with respect to asenapine maleate.

In step c) of this first process for preparing Form G of asenapine maleate, the salt is recovered as a solid product. This step can be accomplished by methods known to those skilled in the art for the separation of a crystallized solid from the mother liquor, for example by filtration, with or without the assistance of pressure and/or vacuum, or by centrifugation. The collected solid is then washed with at least a solvent, commonly the same used in the previous steps of the process, as known in the art, and dried. Drying can be carried out by well known methods, for example by oven-drying with or without the assistance of vacuum.

Alternatively, Form G of asenapine maleate can be prepared according to a second process, comprising steps d) to h) set forth above.

Step d) of this process consists in suspending asenapine maleate in an alcohol at a suitable temperature, preferably comprised between about 0° C. to about 30° C. The alcohols that can be used, and the preferred ones, are the same as defined in step a) of the first process. Preferably, asenapine maleate is added to the alcohol in a ratio of about 1:2.5 to about 1:5 weight/volume.

In step e), the suspension produced in step d) is heated until dissolution of asenapine maleate is achieved. Preferably, the heating temperature is about the reflux temperature of the alcohol employed.

In step f), the thus obtained solution is seeded with Form G of asenapine maleate. Preferably, the seed is added in a weight ratio of about 0.5% to about 1.0% with respect to asenapine maleate to be crystallized; preferably, seeding occurs at a temperature of about 5° C. to about 10° C. below the reflux temperature of the alcohol employed.

In step g), the solution is cooled down (or allowed to cool down) to a temperature that causes the crystallization of Form G, preferably a temperature comprised in the range of about 0° C. to about 30° C.

The final step of this second process, h), consists in recovering Form G of asenapine maleate; this step is carried out following the same procedures described for step c) above.

Form G1 of asenapine maleate has an XRPD spectrum and a DSC thermogram as depicted respectively in FIG. 3 and FIG. 4.

Form G1 of asenapine maleate is characterized by an XRPD pattern comprising peaks at 10.1°, 10.7°, 12.1°, 17.1°, 20.0°, 22.4°, and 24.4° 2θ and by a DSC thermogram showing an intense endothermic feature between 112.8 and 144.2° C.

Form G1 of asenapine maleate can be prepared according to a first process, comprising steps i) to l) set forth above.

Step i) consists in suspending asenapine maleate in an alcohol at a temperature preferably comprised between about 0° C. to about 30° C. The alcohols that can be used, and the preferred ones, are the same as defined in step a) above. Preferably, asenapine maleate is added to the alcohol in a ratio of about 1:3 to about 1:5 weight/volume.

In step j), the suspension produced in step i) is heated until dissolution of asenapine maleate is achieved. Preferably, the heating temperature is about the reflux temperature of the alcohol employed.

In step k), the thus obtained solution is cooled (or allowed to cool) down to a temperature that causes Form G1 to crystallize, preferably comprised in the range of about 10° C. to about 30° C.

The final step of this process, l), consists in recovering Form G1 of asenapine maleate, following the same procedures described for step h) above.

In a variant of the process for obtaining Form G1 of asenapine maleate, a further step, k'), is carried out between steps j) and k). In this variant, the solution obtained in step j) is seeded with Form G1 of asenapine maleate (obtained, e.g., with steps i) to l) above). Preferably, the seed is added in a weight ratio of about 0.5% to about 1.0% with respect to asenapine maleate to be crystallized; preferably, seeding occurs at a temperature of about 5° C. to about 10° C. below the reflux temperature of the alcohol employed. The process is then completed with steps k) and l) described above.

Form G2 of asenapine maleate has an XRPD spectrum and a DSC thermogram as depicted respectively in FIG. 5 and FIG. 6.

Form G2 of asenapine maleate is characterized by an XRPD pattern comprising peaks at 6.6°, 9.2°, 10.4°, 13.2°, 16.8°, 18.5°, 20.1°, 21.2°, and 21.8° 2 and by a DSC thermogram showing an intense endothermic feature between 127.2 and 149.6° C.

Form G2 of asenapine maleate can be prepared according to a first process, comprising steps m) to p) set forth above.

Step m) consists in suspending asenapine maleate in a mixture toluene/tetrahydrofuran, at a temperature preferably comprised in the range of about 0° C. to about 30° C. Preferably, the toluene/tetrahydrofuran ratio is comprised between about 0.6:1 to about 1.5:1 volume/volume. Preferably, asenapine maleate is added to the toluene/tetrahydrofuran mixture in a ratio of about 1:3 to about 1:5 weight/volume.

Step n) consists in heating the suspension until dissolution of asenapine maleate is achieved, obtaining a clear solution. Preferably, the temperature is about the reflux temperature of the toluene/tetrahydrofuran mixture.

In step o), the thus obtained solution is cooled (or allowed to cool) down to a temperature that causes Form G2 to crystallize, preferably comprised in the range of about 10° C. to about 30° C.

The final step of this process, p), consists in recovering Form G2 of asenapine maleate, following the same procedures described for step h) above.

Alternatively, Form G2 of asenapine maleate can be prepared according to a second process, comprising steps q) to u) set forth above.

Step q) of this process consists in suspending asenapine maleate in an alcohol at a suitable temperature, preferably in the range of about 0° C. to about 30° C. The alcohols that can be used, and the preferred ones, are the same as defined in step a) above. Preferably, asenapine maleate is added to the alcohol in a ratio of about 1:3 to about 1:5 weight/volume.

Step r) consists in heating the suspension until dissolution of asenapine maleate is achieved. Preferably, the temperature is about the reflux temperature of the alcohol employed.

Step s) consists in seeding the thus obtained solution with Form G2 of asenapine maleate. Preferably, the seed is added in a weight ratio of about 0.5% to about 1.0% with respect to asenapine maleate to be crystallized; preferably, seeding occurs at a temperature of about 5° C. to about 10° C. below the reflux temperature of the alcohol employed.

In step t), the solution is cooled down (or allowed to cool down) to a temperature that causes the crystallization of Form G2, preferably a temperature comprised in the range of about 0° C. to about 30° C.

The final step of this process, u), consists in recovering Form G1 of asenapine maleate; this step is carried out following the same procedures described for step h) above.

These forms of asenapine maleate have been found to be stable at room temperature, reproducible, and stable under mechanical stresses like a jet mill micronization process. They can be prepared with efficient and economic processes particularly suited to large-scale preparation. Further, they can be used for obtaining asenapine maleate with a HPLC chemical purity higher than 99.5%, suitable for pharmaceutical dosage forms. These forms of asenapine maleate can be used, admixed with pharmaceutically acceptable excipients, in the preparation of pharmaceutical formulations. The latter are conveniently prepared as pharmaceutical dosage forms, in particular in the form of a discrete article such as a tablet, capsule, pill, powder, granule, pellet, lozenge, pastille, elixir, syrup, solution, suspension, emulsion, drop, lotion, spray, tincture, cream, ointment, gel, unguent, suppository and transdermal devices for oral, enteral, parenteral or topical administrations.

The present invention is further illustrated by means of the examples that follow. In the experimental activities performed by the inventors, samples of asenapine maleate polymorphs have been micronized (when necessary) by means of laboratory micronizer Fluid Jet Mill J-20 (Tecnologia Meccanica srl, Treviolo, Italy), using nitrogen as carrier gas and with the operative conditions of 8 bar Venturi pressure and 5 bar ring pressure.

XRPD analyses have been performed on a APD 2000 Ital Structures diffractometer operating at room temperature, using a CuKα tube (40 kV, 30 mA, λ=1.5406 Å) as the X-ray source. Data collection has been made in 2θ step scan mode and in Bragg-Brentano configuration, at a scan speed of 0.04°/s in the range from 3° to 40° in θ/2θ. Samples have been prepared for XRPD analyses by accurate grinding, and have been placed in the hollow of an aluminium sampler. The instrument had been previously calibrated by means of zinc oxide, then allowing acquisition of data by means of WinAcq32 software.

DSC thermal analyses have been performed on a Mettler-Toledo Star$^e$ System with open aluminium pans, heating the samples from 30 to 300° C. in a dry nitrogen atmosphere at a rate of 10° C./minute.

Example 1

Preparation of Form G of Asenapine Maleate, First Process

Asenapine maleate, prepared according to the procedure described in U.S. Pat. No. 4,145,434 (10 g, 0.024 mol), is dissolved under stirring at 25° C. in a mixture of 18.5 mL of ethanol and 1.9 mL of water. Sodium polyoxotungstate monohydrate ($Na_6W_{12}O_{39}.H_2O$, 0.5 g) is added in order to start crystallization of the title compound. The solid material is filtered, washed with ethanol and oven-dried at 60° C. under reduced pressure, thus affording asenapine maleate (7.5 g, 75% yield) in the non-solvate Form G, having a water content lower than 0.1% (Karl-Fischer titration) and an XRPD spectrum and a DSC thermogram as depicted respectively in FIG. 1 and FIG. 2.

Example 2

Preparation of Form G of Asenapine Maleate, Second Process

Asenapine maleate (10 g, 0.024 mol) is suspended under stirring at 25° C. in 30 mL of ethanol. The suspension is heated under stirring up to 78÷80° C. in order to obtain a clear solution, allowed to cool down to 70÷72° C., seeded with Form G of asenapine maleate (0.5 g) obtained in Example 1 and allowed to cool down to 10-15° C. The obtained solid material is filtered, washed with ethanol and oven-dried at 60° C. under reduced pressure, thus affording asenapine maleate (8.1 g, 81% yield) in the non-solvate Form G, having a water content lower than 0.1% (Karl-Fischer titration) and an XRPD spectrum and a DSC thermogram essentially equal to those reproduced in FIG. 1 and FIG. 2, respectively.

Example 3

Preparation of Form G1 of Asenapine Maleate, Base Process

Asenapine maleate (20 g, 0.048 mol) is suspended under stirring at 25° C. in 65 mL of ethanol. The suspension is heated under stirring up to 78÷80° C. in order to obtain a clear solution and then allowed to cool down to 10-15° C. The obtained solid material is filtered, washed with ethanol and oven-dried at 60° C. under reduced pressure, thus affording asenapine maleate (16 g, 80% yield) in the non-solvate Form G1, having a water content lower than 0.1% (Karl-Fischer titration) and an XRPD spectrum and a DSC thermogram as depicted respectively in FIG. 3 and FIG. 4.

Example 4

Preparation of Form G1 of Asenapine Maleate, Variant Process

Asenapine maleate (20 g, 0.048 mol) is suspended under stirring at 25° C. in 65 mL of ethanol. The suspension is heated under stirring up to 78÷80° C. in order to obtain a clear solution, allowed to cool down to 70÷72° C., seeded with Form G1 of asenapine maleate obtained in Example 3, and then allowed to cool down to 10-15° C. The obtained solid material is filtered, washed with ethanol and oven-dried at 60° C. under reduced pressure, thus affording asenapine maleate (16.2 g, 80% yield) in the non-solvate Form G1, having a water content lower than 0.1% (Karl-Fischer titration) and an XRPD spectrum and a DSC thermogram essentially equal to those reproduced in FIG. 3 and FIG. 4, respectively.

Example 5

Preparation of Form G2 of Asenapine Maleate, First Process

Asenapine maleate (10 g, 0.024 mol) is suspended under stirring at 25° C. in 35 mL of a mixture of toluene and tetrahydrofuran (50/50 vol/vol). The suspension is heated under stirring up to 67÷68° C. in order to obtain a clear solution and then allowed to cool down to 10-15° C. The obtained solid material is filtered, washed with toluene and oven-dried at 60° C. under reduced pressure, thus affording asenapine maleate (7.5 g, 75% yield) in the non-solvate Form G2, having a water content lower than 0.1% (Karl-Fischer titration) and an XRPD spectrum and a DSC thermogram as depicted respectively in FIG. 5 and FIG. 6.

Example 6

Preparation of Form G2 of Asenapine Maleate, Second Process

Asenapine maleate (10 g, 0.024 mol) is suspended under stirring at 25° C. in 35 mL of ethanol. The suspension is heated under stirring up to 78÷80° C. in order to obtain a clear solution, allowed to cool down to 70÷72° C., seeded with Form G2 of asenapine maleate obtained in Example 5 and then allowed to cool down to 10-15° C. The obtained solid material is filtered, washed with ethanol and oven-dried at 60° C. under reduced pressure, thus affording asenapine maleate (7.7 g, 77% yield) in the non-solvate Form G2, having a water content lower than 0.1% (Karl-Fischer titration) and an XRPD spectrum and a DSC thermogram essentially equal to those reproduced in FIG. 5 and FIG. 6, respectively.

Example 7

Micronization of Forms G, G1 and G2

Samples (2-3 g) of the polymorphic forms obtained in Examples 1 to 6 are micronized by means of a laboratory micronizer Fluid Jet Mill J-20 (Tecnologia Meccanica srl, Treviolo, Italy), using nitrogen as carrier gas and with the operative conditions of 8 bar Venturi pressure and 5 bar ring pressure. No changes in the XRPD patterns of the sample are detected after the process, thus confirming the mechanical stability of the polymorphs of the invention to a micronization unit.

The invention claimed is:
1. Anhydrous crystalline form of asenapine maleate characterized by an XRPD pattern comprising peaks at 10.1°, 10.7°, 12.1°, 17.1°, 20.0°, 22.4°, and 24.4° 2θ, each angle value having an approximation of ±0.2° 2θ, and a DSC thermogram, obtained at a scanning rate of 10° C./min under inert atmosphere, showing an intense endothermic feature between 112.8 and 144.2° C., each temperature value having an approximation of ±0.5° C.

2. Anhydrous crystalline form of asenapine maleate characterized by an XRPD pattern comprising peaks at 4.5°, 8.7°, and 27.7° 2θ, each angle value having an approximation of ±0.2° 2θ, and a DSC thermogram, obtained at a scanning rate of 10° C./min under inert atmosphere, showing a first endothermic feature between 116.8 and 129.2° C. and a second endothermic feature between 134.3 and 145.4° C., each temperature value having an approximation of ±0.5° C.

3. Anhydrous crystalline form of asenapine maleate characterized by an XRPD pattern comprising peaks at 6.6°, 9.2°, 10.4°, 13.2°, 16.8°, 18.5°, 20.1°, 21.2°, and 21.8° 2θ, each angle value having an approximation of ±0.2° 2θ, and a DSC thermogram, obtained at a scanning rate of 10° C./min under inert atmosphere, showing an intense endothermic feature between 127.2 and 149.6° C., each temperature value having an approximation of ±0.5° C.

4. Process for preparing the form of asenapine maleate of claim 1, comprising the steps of:
   i) suspending asenapine maleate in an alcohol in a weight/volume ratio comprised between 1:3 and 1:5;
   j) heating the suspension in order to obtain a clear solution;
   k) cooling down the solution in order for said form of asenapine maleate to crystallize; and
   l) recovering the solid product.

5. The process of claim 4, comprising, between steps j) and k), a further step k'), consisting in seeding the solution obtained in step j) with said form of asenapine maleate.

6. The process of claim 5 in which, in said step k'), the seed of said form of asenapine maleate is added in a weight ratio of 0.5% to 1.0% with respect to asenapine maleate to be crystallized.

7. Process for preparing the form of asenapine maleate of claim 2, comprising the steps of:
   a) dissolving asenapine maleate in a solvent that is a mixture of water and an alcohol;
   b) adding a polyoxotungstate as seed; and
   c) recovering the solid product.

8. The process of claim 7 in which, in step a), asenapine maleate is dissolved in the mixture of water and alcohol at a weight/volume ratio comprised between 1:1 and 1:2.

9. The process of claim 7 in which said polyoxotungstate has the formula $M_6W_{12}O_{39} \cdot nH_2O$, wherein M is an alkali metal cation selected among lithium, sodium and potassium.

10. The process of claim 7, in which said polyoxotungstate is added in a weight ratio of 0.5% to 1.0% with respect to asenapine maleate.

11. Process for preparing the form of asenapine maleate of claim 2, comprising the steps of:
   d) suspending asenapine maleate in an alcohol;
   e) heating the suspension in order to obtain a clear solution;
   f) seeding with said form of asenapine maleate;
   g) cooling down the solution in order for said form of asenapine maleate to crystallize; and
   h) recovering the solid product.

12. The process of claim 11 in which, in step d), asenapine maleate is added to the alcohol in a weight/volume ratio comprised between 1:2.5 and 1:5.

13. The process of claim 11 in which, in step f), the seed is added in a weight ratio of 0.5% to 1.0% with respect to asenapine maleate to be crystallized.

14. The process of claim 11 in which said step f) is carried out at a temperature of 5° C. to 10° C. below the reflux temperature of the alcohol employed.

15. Process for preparing the form of asenapine maleate of claim 3, comprising the steps of:
   m) suspending asenapine maleate in a mixture toluene/tetrahydrofuran in a weight/volume ratio comprised between 1:3 and 1:5;
   n) heating the suspension in order to obtain a clear solution;
   o) cooling down the solution in order for said form of asenapine maleate to crystallize; and
   p) recovering the solid product.

16. The process of claim 15, in which the toluene/tetrahydrofuran ratio in said mixture is comprised between 0.6:1 to 1.5:1 volume/volume.

17. Process for preparing the form of asenapine maleate of claim 3, comprising the steps of:
   q) suspending asenapine maleate in an alcohol in a weight/volume ratio comprised between 1:3 and 1:5;
   r) heating the suspension in order to obtain a clear solution;
   s) seeding with said form of asenapine maleate;
   t) cooling down the solution in order for said form of asenapine maleate to crystallize; and
   u) recovering the solid product.

18. The process of claim 17 in which, in said step s), the seed of said form of asenapine maleate is added in a weight ratio of 0.5% to 1.0% with respect to asenapine maleate to be crystallized.

19. The process of claim 4, in which said alcohol is selected from the group consisting of methanol, ethanol, 1-propanol, 2-propanol, 1-butanol, 2-butanol and their mixtures.

20. The process of claim 4, in which said steps of suspending asenapine maleate in an alcohol take place at a temperature comprised between 0° C. and 30° C.

21. A pharmaceutical formulation comprising a crystalline form of asenapine maleate according to claim 1 and at least one pharmaceutically acceptable excipient.

22. A pharmaceutical formulation comprising a crystalline form of asenapine maleate according to claim 2 and at least one pharmaceutically acceptable excipient.

23. A pharmaceutical formulation comprising a crystalline form of asenapine maleate according to claim 3 and at least one pharmaceutically acceptable excipient.

24. The process of claim 7, in which said alcohol is selected from the group consisting of methanol, ethanol, 1-propanol, 2-propanol, 1-butanol, 2-butanol and their mixtures.

25. The process of claim 11, in which said alcohol is selected from the group consisting of methanol, ethanol, 1-propanol, 2-propanol, 1-butanol, 2-butanol and their mixtures.

26. The process of claim 17, in which said alcohol is selected from the group consisting of methanol, ethanol, 1-propanol, 2-propanol, 1-butanol, 2-butanol and their mixtures.

27. The process of claim 7, in which said step of dissolving asenapine maleate in a water/alcohol mixture takes place at a temperature comprised between 0° C. and 30° C.

28. The process of claim 11, in which said step of suspending asenapine maleate in an alcohol takes place at a temperature comprised between 0° C. and 30° C.

29. The process of claim 15, in which said step of suspending asenapine maleate in a mixture toluene/tetrahydrofuran takes place at a temperature comprised between 0° C. and 30° C.

30. The process of claim 17, in which said step of suspending asenapine maleate in an alcohol takes place at a temperature comprised between 0° C. and 30° C.

31. The process of claim 5, in which step k') is carried out at a temperature of 5° C. to 10° C. below the reflux temperature of the alcohol employed.

32. The process of claim 17, in which step s) is carried out at a temperature of 5° C. to 10° C. below the reflux temperature of the alcohol employed.

* * * * *